(12) United States Patent
Hynes et al.

(10) Patent No.: US 11,234,804 B2
(45) Date of Patent: Feb. 1, 2022

(54) STENT INCLUDING ANTI-MIGRATION CAPABILITIES

(71) Applicant: BOSTON SCIENTIFIC SCIMED, INC., Maple Grove, MN (US)

(72) Inventors: Martin Hynes, Galway (IE); Martyn G. Folan, Galway (IE); David R. Wulfman, Minneapolis, MN (US); Thomas M. Keating, Galway (IE); Matthew Montague, Galway (IE); Damien V. Nolan, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 211 days.

(21) Appl. No.: 16/718,759

(22) Filed: Dec. 18, 2019

(65) Prior Publication Data

US 2020/0121439 A1    Apr. 23, 2020

Related U.S. Application Data

(63) Continuation of application No. 15/807,141, filed on Nov. 8, 2017, now Pat. No. 10,531,941.

(60) Provisional application No. 62/419,820, filed on Nov. 9, 2016.

(51) Int. Cl.
| | |
|---|---|
| *A61F 2/90* | (2013.01) |
| *A61F 2/00* | (2006.01) |
| *A61F 2/07* | (2013.01) |
| *A61F 2/04* | (2013.01) |

(52) U.S. Cl.
CPC ............. *A61F 2/0077* (2013.01); *A61F 2/07* (2013.01); *A61F 2/90* (2013.01); *A61F 2002/044* (2013.01); *A61F 2002/045* (2013.01); *A61F 2210/0004* (2013.01); *A61F 2230/001* (2013.01); *A61F 2230/008* (2013.01); *A61F 2230/0078* (2013.01); *A61F 2250/0031* (2013.01); *A61F 2250/0039* (2013.01)

(58) Field of Classification Search
CPC ..... A61F 2/07; A61F 2/0077; A61F 2002/045
See application file for complete search history.

(56) References Cited

U.S. PATENT DOCUMENTS

| | | |
|---|---|---|
| 5,167,614 A | 12/1992 | Tessmann et al. |
| 6,805,898 B1 | 10/2004 | Wu et al. |
| 6,918,927 B2 | 7/2005 | Bates et al. |

(Continued)

*Primary Examiner* — Suba Ganesan
(74) *Attorney, Agent, or Firm* — Seager, Tufte & Wickhem, LLP

(57) ABSTRACT

An example medical device for treating a body lumen is disclosed. The medical device includes an expandable scaffold including first and second regions, each of the first and second regions include a plurality of interstices located therein. The medical device also includes a covering spanning each of the plurality of interstices of the first region. The second region is free of the covering. A biodegradable gripping material is disposed on an outer surface of the covering. Further, the expandable scaffold is configured to shift from a collapsed state to an expanded state and the second region is configured to contact an inner surface of the body lumen in the expanded state. Additionally, the gripping material is designed to initially prevent migration of the expandable scaffold upon implantation in the body lumen until the second region is secured to the inner surface of the body lumen.

20 Claims, 9 Drawing Sheets

(56) References Cited

U.S. PATENT DOCUMENTS

| | | |
|---|---|---|
| 7,041,127 B2 | 5/2006 | Ledergerber |
| 8,435,283 B2 | 5/2013 | Jordan et al. |
| 8,444,688 B2 | 5/2013 | Sherry |
| 8,449,602 B2 | 5/2013 | Lye et al. |
| 2007/0179599 A1 | 8/2007 | Brodbeck et al. |
| 2008/0033522 A1 | 2/2008 | Grewe et al. |
| 2009/0005860 A1 | 1/2009 | Gale et al. |
| 2009/0076591 A1 | 3/2009 | Girton et al. |
| 2009/0187240 A1 | 7/2009 | Clerc et al. |
| 2011/0172760 A1 | 7/2011 | Anderson |
| 2012/0283811 A1 | 11/2012 | Neilan |
| 2013/0268063 A1 | 10/2013 | Firstenberg et al. |
| 2014/0074219 A1 | 3/2014 | Hingston et al. |
| 2014/0277395 A1 | 9/2014 | Firstenberg et al. |
| 2015/0045876 A1* | 2/2015 | Clerc ................ A61L 31/10 623/1.38 |
| 2015/0051693 A1* | 2/2015 | Bertolino ............ B29C 66/742 623/1.13 |
| 2015/0157767 A1 | 6/2015 | Edick |
| 2015/0282955 A1 | 10/2015 | Guler et al. |

\* cited by examiner

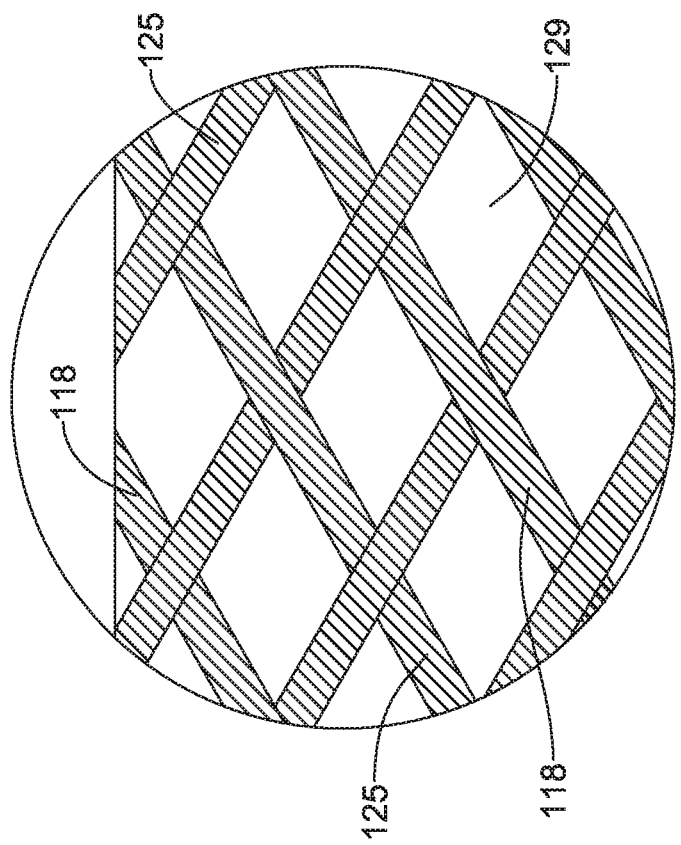
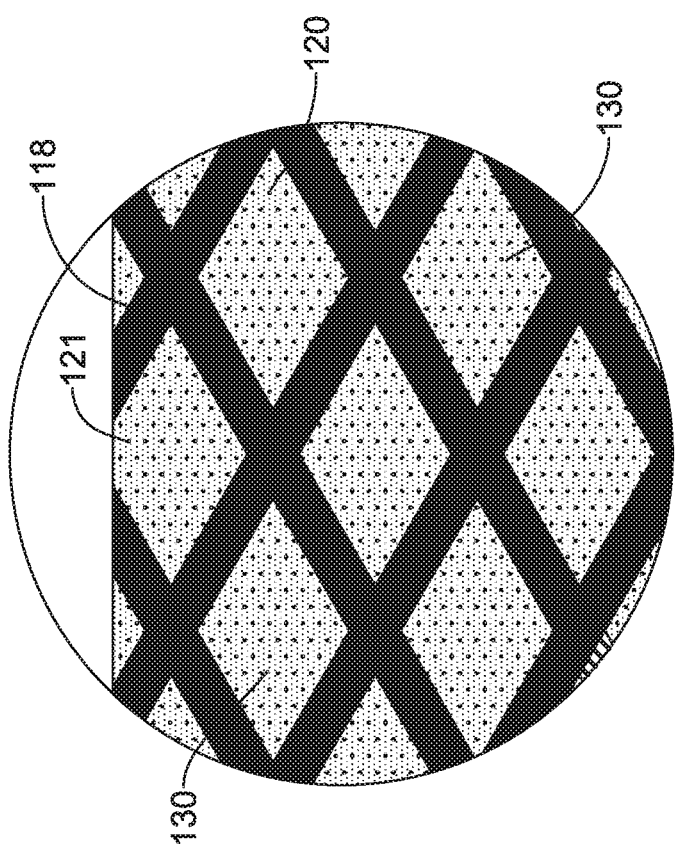
FIG. 5A
FIG. 5B

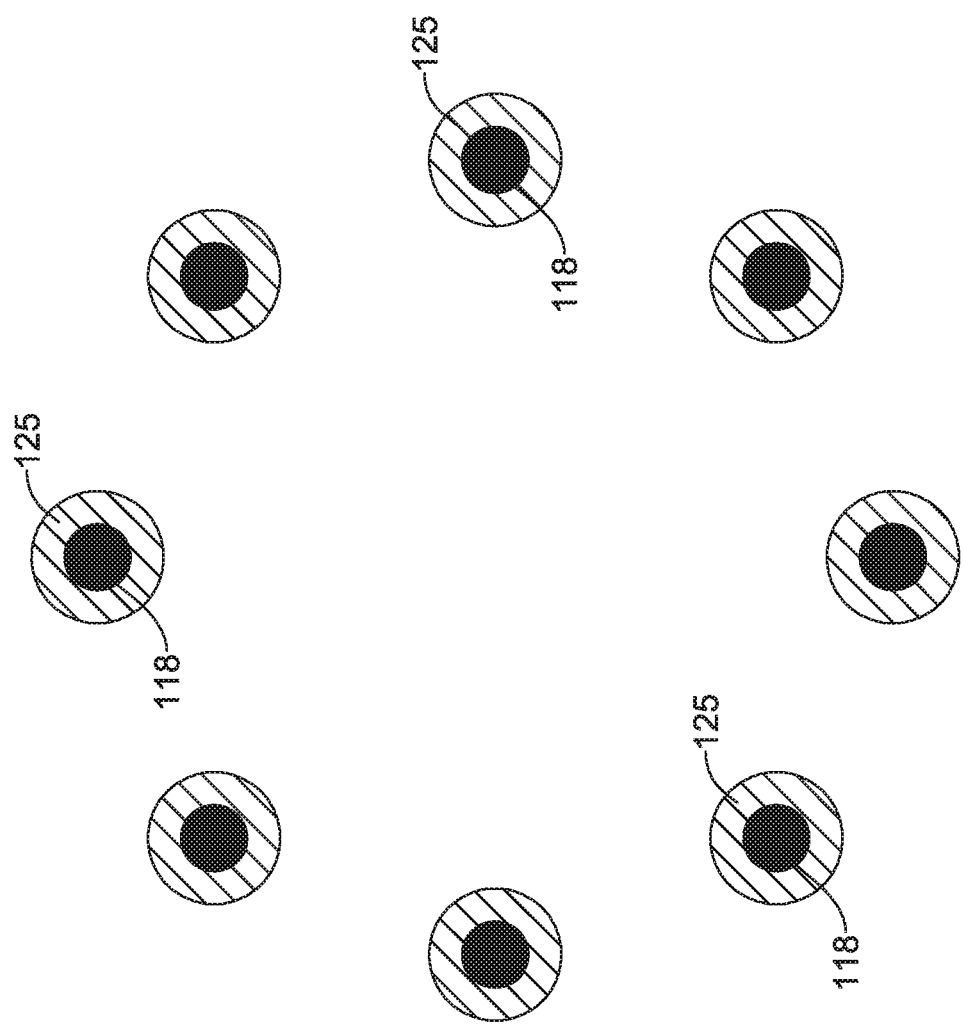

STENT INCLUDING ANTI-MIGRATION CAPABILITIES

CROSS-REFERENCE TO RELATED APPLICATIONS

This application is a continuation of U.S. patent application Ser. No. 15/807,141, filed Nov. 8, 2017, which claims priority under 35 U.S.C. § 119 to U.S. Provisional Application Ser. No. 62/419,820, filed Nov. 9, 2016, the entirety of which is incorporated herein by reference.

TECHNICAL FIELD

The present disclosure pertains to medical devices, and methods for manufacturing medical devices. More particularly, the present disclosure pertains to examples of expandable stents having anti-migration capabilities and methods for manufacturing and using such devices.

BACKGROUND

Implantable medical devices (e.g., expandable stents) may be designed to treat strictures in a body lumen and/or provide a fluid pathway for digested material, blood, or other fluid to flow therethrough following a medical procedure. Some medical devices may include radially or self-expanding stents which may be implanted transluminally via an endoscope. Additionally, some stents may be implanted in a variety of body lumens such as the esophageal tract, the gastrointestinal tract (including the intestine, stomach and the colon), tracheobronchial tract, urinary tract, biliary tract, vascular system, etc.

In some instances it may be desirable to design stents to include sufficient flexibility while maintaining sufficient radial force to open the body lumen at the treatment site. However, in some stents, the compressible and flexible properties that assist in stent delivery may also result in a stent that has a tendency to migrate from its originally deployed position. For example, stents that are designed to be positioned in the esophageal or gastrointestinal tract may have a tendency to migrate due to peristalsis (i.e., the involuntary constriction and relaxation of the muscles of the esophagus, intestine, and colon which push the contents of the canal therethrough). Additionally, the generally moist and inherently lubricious environment of the esophagus, intestine, colon, etc. further contributes to a stent's tendency to migrate when deployed therein. One method to reduce stent migration may include exposing bare metal portions of the stent to the tissue of the body lumen. The stent scaffold may provide a structure that promotes tissue ingrowth into the interstices or openings thereof. The tissue ingrowth may anchor the stent in place and reduce the risk of stent migration.

Additionally, while it is important to design stents that reduce the degree to which a stent migrates within a body lumen, it also important to design stents that may be easily removed and/or re-positioned from the body lumen post-deployment. Stents including bare portions (i.e., uncovered portions) designed to promote tissue ingrowth (e.g., to reduce stent migration as described above) may also be more difficult to remove once the tissue has anchored the stent in the body lumen. One method to reduce the force necessary to remove a stent from a body lumen may include covering a portion of the stent, thereby creating a physical barrier between the body lumen and the outer surface of the stent (e.g., reducing the surface area of the stent which may anchored via tissue ingrowth). However, covered stents may be more prone to migration than bare stents (as discussed above).

Therefore, in some instances it may be desirable to design a stent which includes both a covered portion (to ease removability) and a non-covered (e.g., bare) portion (to reduce the stent's tendency to migrate). Examples of the medical devices including covered and non-covered portions are disclosed herein.

BRIEF SUMMARY

This disclosure provides design, material, manufacturing method, and use alternatives for medical devices. An example medical device for treating a body lumen includes an expandable scaffold including a first region and a second region, each of the first and second regions including a plurality of interstices located therein. The medical device also includes a covering spanning each of the plurality of interstices of the first region, wherein the second region is free of the covering. The medical device also includes a gripping material disposed on an outer surface of the covering, wherein the gripping material is biodegradable. Further, the expandable scaffold is configured to shift from a collapsed state to an expanded state and the second region is configured to contact an inner surface of the body lumen in the expanded state. Additionally, the gripping material is designed to initially prevent migration of the expandable scaffold upon implantation in the body lumen until the second region is secured to the inner surface of the body lumen via tissue ingrowth into the interstices of the second region.

Alternatively or additionally to any of the embodiments above, wherein the tissue ingrowth into the interstices of the second region is due to a hyperplasic tissue response.

Alternatively or additionally to any of the embodiments above, the wherein the gripping material is configured to degrade over a first time period.

Alternatively or additionally to any of the embodiments above, wherein the securement of the second region to the inner surface of the intestine occurs over a second time period.

Alternatively or additionally to any of the embodiments above, wherein the second time period occurs before the first time period.

Alternatively or additionally to any of the embodiments above, wherein the second time period overlaps with the first time period.

Alternatively or additionally to any of the embodiments above, wherein the second time period is between 4 to 18 days.

Alternatively or additionally to any of the embodiments above, further comprising a third region positioned on an end of the scaffold opposite the second region, wherein the third region is free of the covering and wherein the third region includes a flared portion.

Alternatively or additionally to any of the embodiments above, wherein the covering is configured to provide a pathway for food to travel therethrough.

Alternatively or additionally to any of the embodiments above, wherein the expandable scaffold has a longitudinal axis and a length along the longitudinal axis and wherein the second region has a length which is between 5-15% of the length of the expandable scaffold.

Alternatively or additionally to any of the embodiments above, wherein the second region includes a flared portion.

Alternatively or additionally to any of the embodiments above, wherein the covering is formed of a biostable material.

Alternatively or additionally to any of the embodiments above, wherein the second region includes an endothelializing material disposed along a surface thereof.

Another example medical device for treating a body lumen includes an expandable scaffold including a first region and a second region, each of the first and second regions including a plurality of struts defining a plurality of interstices located therebetween;

a covering spanning each of the plurality of interstices of the first region, wherein the covering is biostable; and a gripping material disposed on an outer surface of the covering, wherein the gripping material is biodegradable;

wherein the expandable scaffold is configured to shift from a collapsed state to an expanded state, and wherein the second region is configured to contact an inner surface of the body lumen in the expanded state;

wherein the struts of the second region are bare metal and configured to be secured to the inner surface of the body lumen via tissue ingrowth into the interstices of the second region;

wherein the gripping material is designed to initially prevent migration of the expandable scaffold upon implantation in the body lumen until the second region is secured to the inner surface of the body lumen.

Alternatively or additionally to any of the embodiments above, wherein the tissue ingrowth into the interstices of the second region is due to a hyperplasic tissue response.

Alternatively or additionally to any of the embodiments above, wherein the gripping material is configured to degrade over a first time period.

Alternatively or additionally to any of the embodiments above, wherein the securement of the second region to the inner surface of the intestine occurs over a second time period.

Alternatively or additionally to any of the embodiments above, wherein the second time period occurs before the first time period.

Alternatively or additionally to any of the embodiments above, wherein the second time period overlaps with the first time period.

An example method for treating an intestine includes advancing an expandable scaffold to a target site within the intestine, the expandable scaffold including:

a first region and a second region, each of the first and second regions including a plurality of interstices located therein;

a covering spanning each of the plurality of interstices of the first region, and wherein the second region is free of the covering; and a gripping material disposed on an outer surface of the covering, wherein the gripping material is biodegradable;

radially expanding the scaffold from the contracted state to the expanded state such that the second region is configured to contact an inner surface of the intestine in the expanded state;

temporarily securing the inner surface of the first region to the inner surface of the intestine with the gripping material until the second region is secured to the inner surface of the body lumen via tissue ingrowth into the interstices of the second region due to a hyperplastic response.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIG. 1A illustrates a detailed view of a first portion of the stent shown in FIG. 1;

FIG. 1B illustrates a detailed view of a second portion of the stent shown in FIG. 1;

FIG. 5A illustrates a detailed view of a portion of the stent shown in FIG. 5;

FIG. 5B illustrates a detailed view of a portion of the stent shown in FIG. 5;

FIG. 6 illustrates a cross-sectional view along line 6-6 of FIG. 5;

Figure 1:
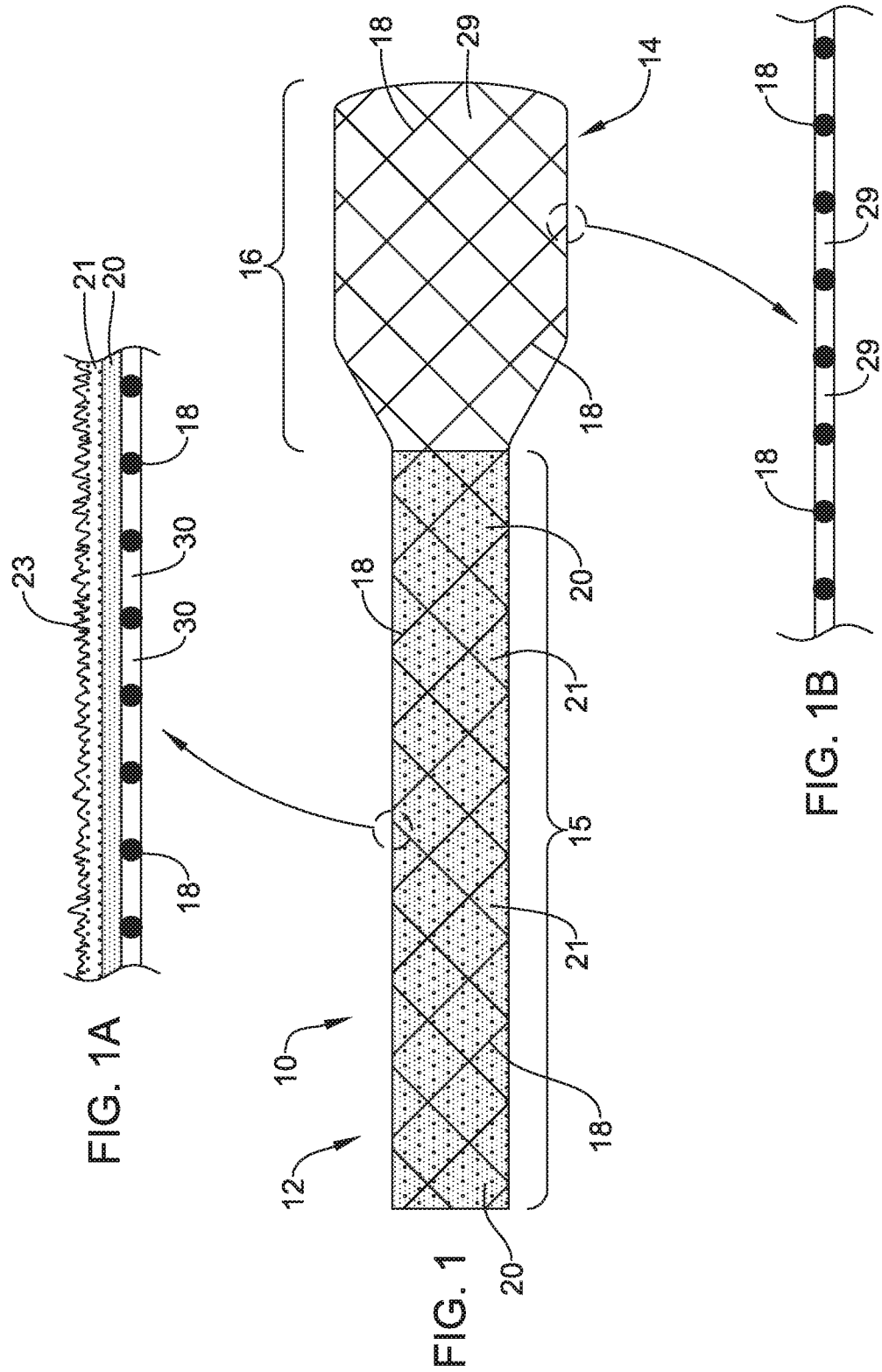
FIG. 1 illustrates an example stent including a covered region and uncovered region.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

As discussed above, implantable medical devices may be designed to treat strictures in a body lumen and/or provide a fluid pathway for digested material, or other material or fluid, to flow therethrough following an invasive medical procedure. Examples disclosed herein may include radially or self-expanding stents. The expandable stents may be implanted transluminally via an endoscope, or another desired delivery means. Additionally, some stents may be implanted in a variety of body lumens such as the esophageal tract, the gastro-intestinal tract including the intestine and the colon, airways, urinary tracts, biliary tract including bile and/or pancreatic ducts, vascular system, etc.

In some instances, it may be desirable to design stents to include sufficient flexibility to be able to conform to the tortuous body lumen during delivery yet sufficient radial force to open the body lumen at the treatment site. However, in some stents, the compressible and flexible properties that assist in stent delivery may also result in a stent that has a tendency to migrate from its originally deployed position. For example, stents that are designed to be positioned in the esophagus or intestine may have a tendency to migrate due to peristalsis (i.e., the involuntary constriction and relaxation of the muscles of the esophagus, intestine, and colon which push the contents of the canal therethrough). Additionally, the generally moist and inherently lubricious environment of the esophagus, intestine, colon, etc. further contributes to a stent's tendency to migrate when deployed therein. One method to reduce stent migration may include exposing bare metal portions of the stent to the tissue of the body lumen. The stent scaffold may provide a structure that promotes tissue ingrowth into the interstices thereof. The tissue ingrowth may anchor the stent in place and reduce the risk of stent migration.

Additionally, while it is important to design stents that reduce the degree to which a stent migrates within a body lumen, it also important to design stents that may be easily removed and/or re-positioned from the body lumen post-deployment. Stents including bare portions (i.e., uncovered portions) designed to promote tissue ingrowth (e.g., to reduce stent migration as described above) may also be more difficult to remove once the tissue has anchored the stent in the body lumen. One method to reduce the force necessary to remove a stent from a body lumen may include covering a portion of the stent, thereby creating a physical barrier between the body lumen and the outer surface of the stent (e.g., reducing the surface area of the stent which may anchored via tissue ingrowth). However, covered stents may be more prone to migration than bare stents (as discussed above). Therefore, in some instances it may be desirable to design a stent which includes both a covered portion and a non-covered (e.g., bare) portion.

FIG. 1 illustrates an example implantable medical device, illustrated as a stent 10. However, although illustrated as a stent, implantable medical device 10 may be any of a number of devices that may be introduced endoscopically, subcutaneously, percutaneously or surgically to be positioned within an organ, tissue, or lumen, such as an intestine, colon, urethra, esophagus, trachea, bronchus, bile duct, blood vessel, or the like. Stent 10 may be configured to be positioned in a body lumen for a variety of medical applications. For example, stent 10 may be used to treat a stricture in a body lumen. Additionally, stent 10 may be used to provide a pathway for food or other digested materials to pass therethrough without directly contacting adjacent tissue. It is contemplated that the examples described herein may be utilized in the gastrointestinal tract, as well as in the esophageal, vascular, urinary, biliary, tracheobronchial, or renal tracts, for example. In some instances, stent 10 (e.g., an intestinal stent, an esophageal stent, a vascular stent, tracheal stent, bronchial stent, etc.) may include an expandable scaffold.

Expandable scaffold of stent 10 may have a first portion 12 and a second portion 14 positioned adjacent to and extending from the first portion 12. In some instances, first portion 12 may extend to a first end of the implantable medical device 10 and second portion 14 may extend to a second end of the implantable medical device 10 opposite the first end. First portion 12 may be attached to second portion 14 along the length of the implantable medical device 10 to form an expandable tubular framework or scaffold with open ends and defining a lumen extending therein. First portion 12 and/or second portion 14 may include a flared portion, if desired. For example, FIG. 1 illustrates second portion 14 having an outer diameter that is greater than the outer diameter of the first portion 12. Additionally, first portion 12 and second portion 14 may extend along a central longitudinal axis of stent 10. In some instances, first portion 12 may be a cylindrical portion having a substantially constant diameter with second portion 14 flaring outward therefrom to the second end of stent 10.

A plurality of strut members 18 may be arranged in a variety of different designs and/or geometric patterns to form the expandable tubular framework or scaffold of stent 10. Numerous designs, patterns and/or configurations for the stent cell openings, strut thicknesses, strut designs, stent cell shapes are contemplated and may be utilized with embodiments disclosed herein. Further, self-expanding stent examples disclosed herein may include stents having one or more strut members 18 combined to form a rigid and/or semi-rigid stent structure. In some examples disclosed herein, the collection of strut members 18 forming a rigid and/or semi-rigid framework structure may be referred to as a scaffold. For example, strut members 18 may be wires or filaments braided, intertwined, interwoven, weaved, knitted, crocheted or the like to form the expandable scaffold or framework of stent 10. The strut members (e.g., wires or filaments) 18 of stent 10 may be configured to self-expand to an expanded diameter when unconstrained. Alternatively, strut members 18 may be formed from a monolithic structure (e.g., a cylindrical tubular member), such as a single, cylindrical tubular laser-cut Nitinol tubular member, in which the remaining portions of the tubular member form the strut members 18. The monolithic structure of stent 10 may be configured to self-expand to an expanded diameter when unconstrained.

Expandable scaffold of stent 10 in at least some examples disclosed herein may be constructed from a variety of materials. For example, expandable scaffold of stent 10 may be constructed from a metal (e.g., Nitinol). In other instances, expandable scaffold of stent 10 may be constructed from a polymeric material (e.g., PET). In yet other instances, expandable scaffold of stent 10 may be constructed from a combination of metallic and polymeric materials. Additionally, expandable scaffold of stent 10 or portions thereof may include a bioabsorbable and/or biodegradable material.

As discussed above, in some instances it may be desirable to design stent 10 to include a covered portion and an uncovered portion. For example, FIG. 1 shows stent 10 including a covered region 15 and an uncovered region 16. For purposes of the discussion herein, first portion 12 of the expandable scaffold of stent 10 may correspond to covered region 15 and second portion 14 of the expandable scaffold of stent 10 may correspond to uncovered region 14.

FIG. 1 further illustrates example stent 10 including one or more layers (e.g., covering, coating, etc.) of material positioned on and/or adjacent to the outer and/or inner surface of strut members 18. For example, FIG. 1 illustrates stent 10 including a first layer 20 (depicted by the smaller dot pattern in FIG. 1) and a second layer 21 (depicted by the larger dot pattern in FIG. 1). In some instances, layer (e.g., covering) 20 and/or layer 21 may be an elastomeric or non-elastomeric material. Covering 20 and/or covering 21 may be formed from a suitable material, such as a biostable material. For example, the layer or covering 20 may be a polymeric material, such as silicone, polytetrafluoroethylene, polyurethane, or the like, or other materials including those disclosed herein. Further, covering 20 may be a biostable material. For purposes of discussion herein, a biostable material may be defined as a material that does not biodegrade.

Additionally, covering 21 may be formed from a suitable material. For example, the layer or covering 21 may be a bioabsorbable and/or biodegradable material. For example, the layer or covering 21 may be a bioresorbable elastomer. In some instances, layer or covering 21 may include a material made from polyglycerol sebacate such as Regnerez® from Secant Medical Components.

FIG. 1A illustrates a detailed view of a portion of the covered region 15 of example stent 10. As shown in FIG. 1A, the covered region 15 of example stent 10 may include one or more layers. For example, FIG. 1A shows example first layer 20 and second layer 21 disposed along strut members 18. First layer 20 may fully cover the covered region 15 of stent, thus extending across or spanning the interstices 30 between struts 18 of first portion 12 of the expandable framework of scaffold of stent 10. As shown in FIG. 1A, layers 20 and 21 may partially surround one or more strut members 18. While FIG. 1A shows layers 20 and 21 extending along the outer surface of strut members 18, it is contemplated that layers 20 and 21 extend along the inner surface of strut members 18 and/or may fully surround one or more strut members 18.

Further, FIG. 1A illustrates layers 20 and 21 may be disposed along strut members 18 such that layers 20 and 21 are positioned radially outward of strut members 18 and extend across interstices or openings 30 between adjacent struts 18. In other words, first layer 20 and/or second layer 21 may be arranged such that layers 20 and 21 are on the outer surface of strut members 18 of stent 10 to fully cover first portion 12 of stent 10, and thus prevent tissue ingrowth into first portion 12 of stent 10. Additionally, FIG. 1A illustrates second layer 21 being positioned radially outward of first layer 20. Second layer 21 may be disposed on at least a portion of an outer surface of first layer 20. In other words, FIG. 1A illustrates that layer 21 may be positioned at an outermost layer of stent 10 such that it contacts the inner surface of a body lumen in which stent 10 may be deployed.

FIG. 1A further illustrates that layer 21 may be configured to include a textured and/or roughened surface 23 designed to contact and engage with the inner surface of an example body lumen engaged therewith. For example, in some instances, layer 21 may be designed such that textured surface 23 may temporarily anchor the covered portion 15 of stent 10 along the inner surface of an example body lumen. Additional examples of the textured surface 23 and its method of use will be described in greater detail below.

FIG. 1B illustrates that the stent struts 18 forming uncovered region 16 are free from (i.e., devoid of) layers and/or a covering. For example, FIG. 1B shows that stent struts 18 are free from layer 20 and/or layer 21 previously described with respect to covered portion 15. Thus, tissue ingrowth may be promoted into interstices between struts 18 of second portion 14.

As described above, it may be desirable to design a stent which includes both a covered portion and an uncovered portion. It can further be appreciated that designing a stent to include both a covered portion and uncovered portion may allow the stent to be easily removable/repositionable while also reducing the stent's tendency to migrate along a body lumen. In other words, at least some example stent designs disclosed herein may be customized to include both a covered portion and an uncovered portion having particular design parameters (e.g., lengths, coverings/layers, bare sections, etc.) which complement each other to achieve a stent which reduces the tendency of the stent to migrate while also permitting the stent to be readily removable/repositionable should the need arise. The particular design features of the covered region 15 and uncovered region 16 will be described below.

As discussed above, it can be appreciated that layer 21 (including the roughed surface 23) described above may be configured to prevent stent 10 from shifting longitudinally or migrating relative to an inner surface of a body lumen when stent 10 is positioned adjacent a target site (e.g., when placed adjacent a stricture in the esophagus or intestine). In some instances, the roughened surface 23 of layer 21 may include a variety of different surface textures and/or features. For example, roughened portion 23 may include a surface roughening, points, spikes, spurs, ribs, bumps, ridges, protuberances, etc. which may be configured to project alongside, partially into and/or through the wall of a body lumen, or otherwise engage the wall of a body lumen, thereby providing some degree of interaction (e.g., surface friction, mechanical interlock, interface, engagement, etc.) between layer 21 and the tissue of the body lumen (e.g., esophagus or intestine). The engagement of the roughened surface 23 of layer 21 with the tissue of the body lumen may initially prevent stent 10 from longitudinally shifting or migrating with respect to the body lumen upon implantation within the body lumen. In some instances, layer 21 including surface texture 23 may be configured to remain engaged with the inner surface of the body lumen, thereby not extending into the wall of a body lumen. Layer 21 (including a surface texture 23) may create friction and/or adhesion with the tissue of the body lumen (e.g., the inner surface of the esophagus or intestine), which may prevent stent 10 from longitudinally shifting or migrating with respect to the body lumen. For example, in some instances surface texture 23 may resemble and/or mimic roughened sandpaper designed to "grip" the inner surface of a body lumen. In some examples, layer 21 may have surface roughness ($R_a$) values from about 0.5 micrometers (μm) to 2.5 μm, or from about 1.0 μm to 2.0 μm, or from about 1.25 μm to 1.80 μm, or about 1.5 μm.

Figure 2:
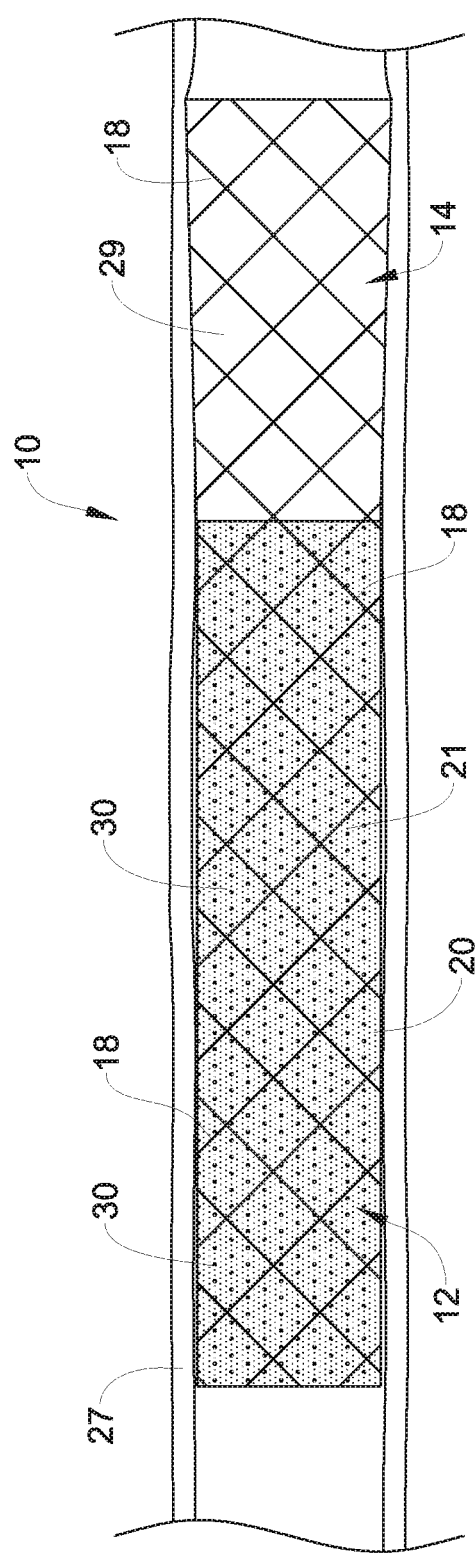
FIG. 2 illustrates the example stent deployed in a body lumen at a first moment in time.

FIG. 2 shows example stent 10 deployed in body lumen 27. As illustrated, upon initial deployment in the body lumen, the flared portion of the second region 14 may apply a radially outward force upon the inner surface of body lumen 27. This radially outward force exerted on the inner surface of body lumen 27 may provide a temporary resistance to migration of stent 10 within the body lumen. Additionally, the flared portion of uncovered region 14 may permit the uncovered region 14 of stent 10 to contact the tissue on the inner surface of body lumen 27. This contact of the bare strut members 18 with the tissue of the inner surface of the body lumen 27 may initiate a hyperplastic response (e.g., tissue ingrowth) that eventually holds the stent in place long term once sufficient tissue ingrowth has occurred. Additionally, it can be appreciated that the roughened surface 23 of covered portion 15 of stent 10 may also be positioned such that it interfaces (e.g., engages) with the inner surface of body lumen 27 upon implantation, and thereby provides an initial resistance to migration of stent 10 until tissue ingrowth occurs in uncovered region 14.

It can be appreciated from the above discussion that the roughened section 23 of layer 21 of stent 10, or the combination of the flared portion of uncovered region 14 and the roughened section 23 of layer 21 of stent 10, may provide an initial, temporary resistance to migration of stent 10 within body lumen 27. It can be further appreciated that the roughened portion 23 of the covered region 12 of stent 10 may only need to resist migration of stent 10 until tissue ingrowth has anchored the uncovered portion 14 of stent 10 to the body lumen 27 (via the hyperplastic response as described above). In other words, upon deployment, covered portion 12 (including roughened layer 23) may temporarily hold stent 10 in place (e.g., resist migration of stent 10) for a time period long enough to permit tissue for the inner surface of body lumen 27 to grow in the interstices 29 arranged between the strut members 18 of the uncovered portion 16 of stent 10. Once enough tissue has grown into the interstices of 29, thereby anchoring (e.g., embedding, locking, gripping, etc.) the struts 18 to the inner surface of the body lumen 27, layer 21 of the covered portion 15 of stent 10 may no longer be necessary to further hold stent 10 in place.

Figure 3:
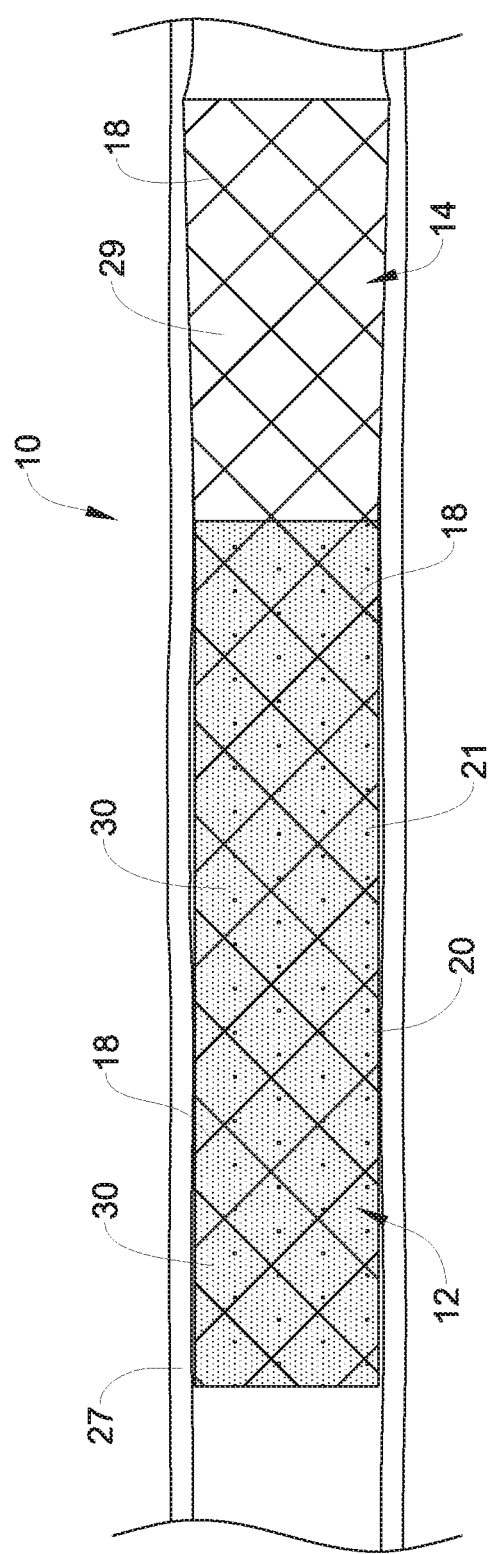
FIG. 3 illustrates the example stent deployed in a body lumen at a second moment in time at a temporal occasion after the first moment in time.
Figure 4:
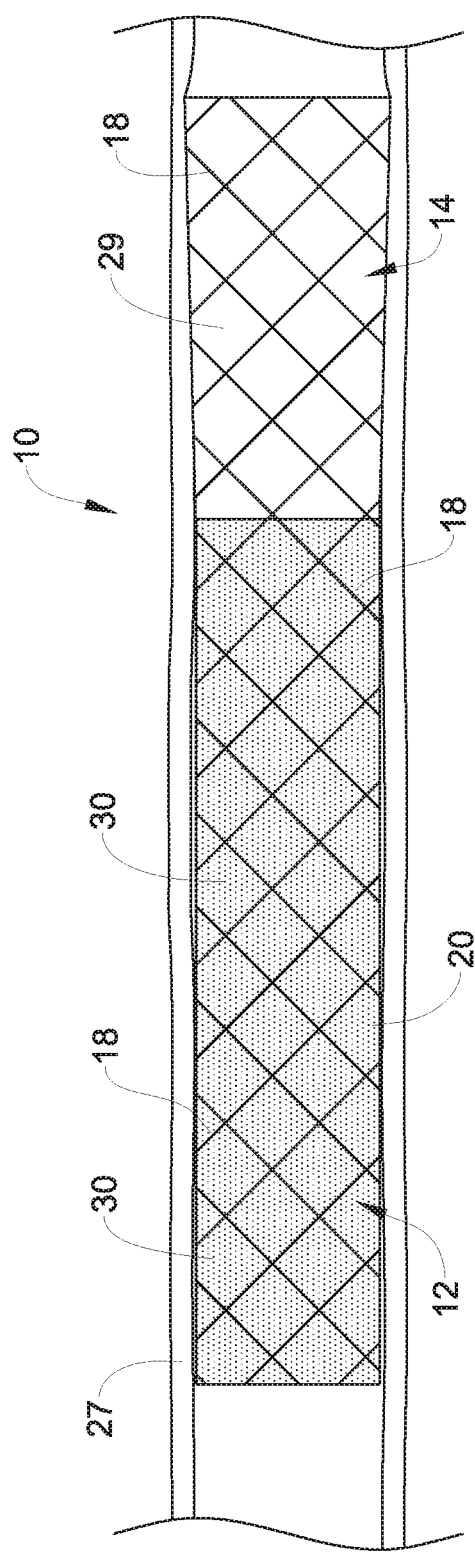
FIG. 4 illustrates the example stent deployed in a body lumen at a third moment in time at a temporal occasion after the second moment in time.

Accordingly, in at least some examples described herein, layer 21 including roughed section 23 (as described with respect to FIG. 1), may be designed to biodegrade over a given time period. For example, FIGS. 3-4 illustrate layer 21 (depicted as the large dot pattern) biodegrading over a given time period. As illustrated, FIG. 3 shows fewer large dots as compared to FIG. 2, while FIG. 4 illustrates the point in time at which layer 21 has completely biodegraded away from stent 10. It can be appreciated from FIGS. 2-4 that as layer 21 biodegrades away from stent 10, it leaves layer 20 (e.g., a silicone covering) as the only remaining layer on covered region 15 of stent 10.

It can be appreciated that layer 20 of stent 10 may span the interstices or openings 30 between the strut members 18 of covered region 15 of stent member 10. In other words, layer 20 may be an unbroken layer of material that spans both the entire length and entire circumference of first portion 12, forming a barrier to prevent tissue ingrowth along covered region 15. Thus, covering layer 20 may extend fully circumferentially around stent 10 at least along the first portion 12 of stent 10, and, in some instances, may extend from one end of stent 10 and fully cover the first portion 12. Further, as described above, the covered region 15 of stent 10 may reduce the percentage of surface area of stent 10 which contacts the vessel wall, thereby reducing the force necessary to remove and/or reposition stent 10.

In some instances, covering layer 20 may be disposed along an outer or inner surface of strut members 18. In other instances, covering 20 may be disposed along both an inner and an outer surface of stent strut members 18. In some of these and in other instances, covering 20 may encapsulate strut members 18 or otherwise have strut members 18 embedded (e.g. partially or fully embedded) therein. Coupling covering 20 to strut members 18 may include thermal bonding, molding, spray coating, dip coating, extruding, adhering, injection molding or the like. Further, the covering layer 20 may span the spaces (e.g., openings, cells, interstices) between struts or filaments 18 of covered region 15 of stent 10.

The covering 20 disclosed herein may be configured such that digested material (e.g., digested food, liquids, etc.) cannot pass from an inner surface of the covering 20 to the outer surface of the covering 20. In other words, when positioned on the outer and/or inner surface of stent 10, the covering may define a pathway that permits food to pass through the inner lumen of stent 10 without leaking from the inner surface to the outer surface of the covering layer 20.

The length of the covered region 12 (as measured along the longitudinal axis of stent 10) may be different as compared to the length of the uncovered region 14 (as measured along the longitudinal axis of stent 10). While it is contemplated that the percentage of covered versus uncovered portions of stent 10 may be in any ratio, it may be desirable to tailor the amount of the covered versus covered portions to optimize the performance features of stent 10. For example, in at least some examples contemplated herein the length of uncovered region 14 may be between 0-25% of the overall length of stent 10 from the first end to the second end of stent 10 (e.g., the overall length being the length of first portion 12 and second portion 14), or may be between 5-15% of the overall length of stent 10, or may be about 10% of the overall length of stent 10.

Additionally, as described above, the time period over which biodegradable layer 21 degrades may be customized based on the desired performance of stent 10. For example, in some examples contemplated herein, the hyperplastic response exhibited by bare stent portion 14 (e.g., the response of tissue ingrowth into and around bare strut members 18) may be about 2 to 20 days, or may be about 4 to 18 days, or may be about 6 to 16 days, or may be about 5 to 15 days, or may be about 7 to 14 days, or may be about 4 to 14 days, or may be about 10 days. Therefore, in some examples, biodegradable layer 21 may be configured to fully degrade over a period of about 50 or more days, or over a period of about 25 or more days, or over a period of about 15 or more days, or over a period of about 10 or more days, or over a period of about 5 or more days, or over a period of about 1 or more days. In some examples, biodegradable layer 21 may be configured to fully degrade over a period of about 4 to 40 days, over a period of about 4 to 30 days, over a period of about 4 to 20 days, or over a period of about 4 to 10 days, over a period of about 10 to 40 days, over a period of about 10 to 30 days, or over a period of about 10 to 20 days.

Furthermore, it can be appreciated that the period over which a hyperplastic response occurs may overlap (e.g., occur contemporaneously) with the period over which the biodegradable layer 21 biodegrades. For example, in some instances the hyperplastic response exhibited by bare stent portion 14 may occur over a time period of about 7-10 days and the period over which biodegradable layer 21 fully biodegrades may be about 5-15 days. Therefore, it can be appreciated that covered portion 12 may hold stent in place long enough to ensure that sufficient tissue ingrowth along the uncovered portion 14 such that uncovered portion 14 has been sufficiently anchored into the tissue of the inner surface of the body lumen. It can be appreciated that many different combinations of time periods for the hyperplastic response of uncovered portion 14 and the biodegrading of layer 14 may be configured for a given stent design.

Additionally, it can be appreciated that stent 10 may be designed such that biodegradable layer 21 may not begin to biodegrade until after the hyperplastic response of the uncovered portion 14 has substantially anchored stent 10 to the body lumen. Further, in some examples, stent 10 may be designed such that biodegradable layer 21 may respond to a trigger which initiates the layer 21 to begin biodegrading. This trigger may be programmed to initiate the breakdown of the biodegradable layer 21 after the hyperplastic response of the uncovered portion 14 has been begun and/or completed. In other words, in some examples, the time period over which layer 21 of the covered portion may be begin to biodegrade may not occur until after the time period in which the hyperplastic response of the covered portion has occurred.

Figure 5:
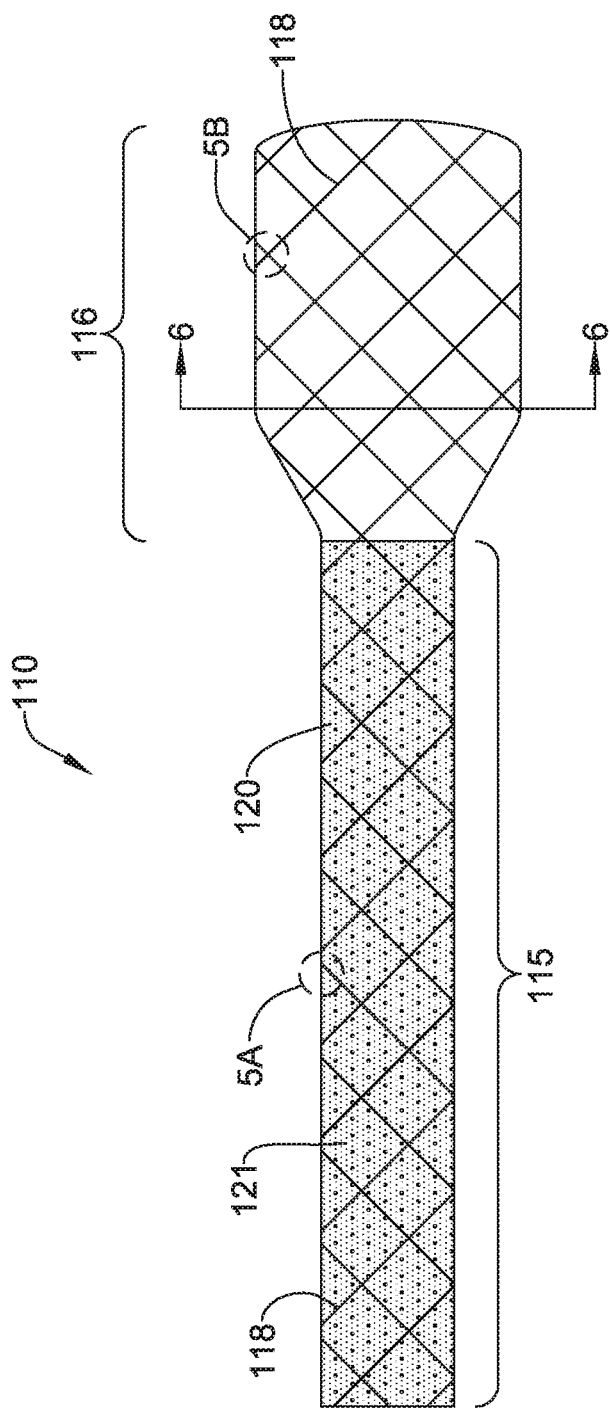
FIG. 5 illustrates another example stent including a covered region and an uncovered region.

FIG. 5 illustrates another example stent 110. Stent 110 may be similar in form and functionality to stent 10, the portions thereof described above. For example, stent 110 may include stent struts 118, covered region 115 and an uncovered region 116. Covered region 115 may include a covering layer 120 over which a biodegradable layer 121 is disposed (similar to covering layer 20 and biodegradable layer 21 described above).

However, in some examples, such as that shown in the detailed view of covered portion 115 in FIG. 5A, the covering 120 and biodegradable layer 121 disposed thereon may include different thicknesses within cells 130 (i.e. diamond shaped areas between the struts). Designing stent 110 to include different thicknesses for the covering 120 and/or biodegradable layer 121 (along with the biodegradable layer 121 material choice) may influence the specific rate of degradation of biodegradable layer 121. Additionally, including a combination of materials (e.g., degradable/biodegradable, etc.) within cells 130 may permit control of both the rate at which ingrowth occurs and the specific shape of the area which degrades (and hence, the specific area into which the ingrowth occurs). Alternatively, including a combination of materials (e.g., degradable/biodegradable, etc.) within cells 130 may dictate the specific pattern of ingrowth which occurs within cells 130.

Furthermore, FIG. 5B illustrates that stent struts 118 of the uncovered portion 116 of the example stent shown in FIG. 5 may include a growth promoting (e.g., endothelializing) material 125 disposed along a portion or the entire surface area of stent struts 118. For example, the growth promoting material 125 may be applied to the outer surface stent struts 118 of uncovered portion 116, thereby being positioned to contact the tissue of the inner surface of a body lumen when uncovered portion 116 is expanded radially outward. However, it is also contemplated that growth promoting material 125 may entirely surround the strut members 118 of uncovered portion 116. For example, FIG. 6 shows a cross-sectional view of uncovered region 116 along line 6-6 of FIG. 5. As illustrated in FIG. 6, strut members 118 are fully surrounded by growth promoting material 125. However, as described above, it is contemplated that in some examples growth promoting material 125 may be disposed along only a portion of strut members 118. Additionally, it can be appreciated that growth promoting material may be designed to aid a hyperplastic response of the uncovered portion of stent 110, as described with respect to the examples provided above, to promote tissue ingrowth into or through interstices 129 between strut members 118 of uncovered portion 116.

Figure 7:
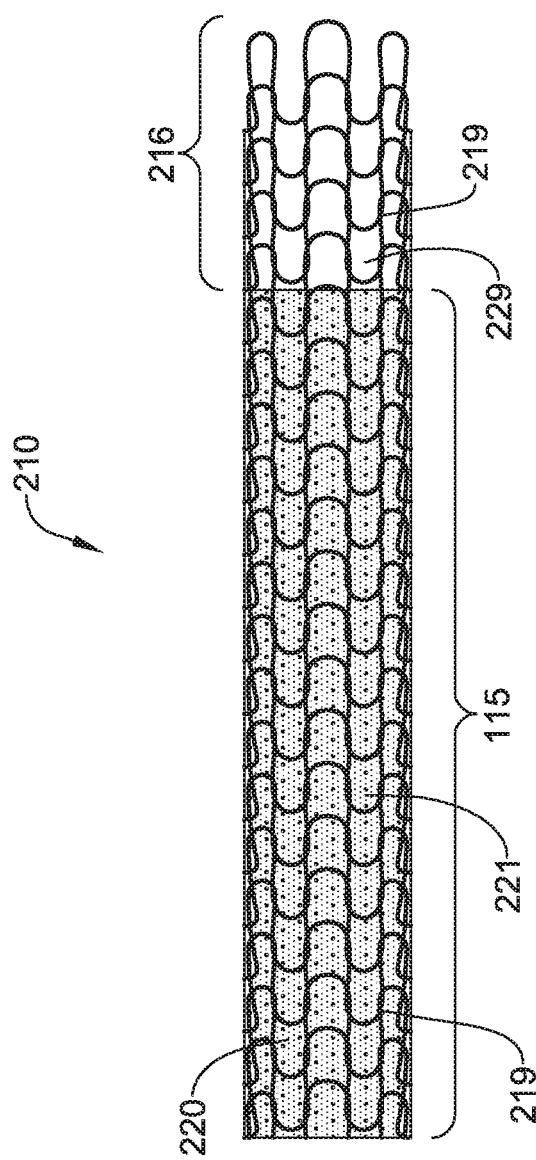
FIG. 7 illustrates another example stent including a covered region and an uncovered region.

FIG. 7 illustrates another example stent 210. Stent 210 may be similar in form and functionality to example stents the portions thereof described above. For example, stent 210 may include a covered region 215 and an uncovered region 216. Further, first, covered region 215 may extend to a first end of the stent 210 and second, uncovered region 216 may extend to a second end of stent 210. Additionally, first, covered region 215 and second, uncovered region 216 may extend along the length of the stent 210 to form an expandable tubular framework with open ends and defining a lumen extending therein. First, covered region 215 and/or second, uncovered region 216 may have a flared end portion, if desired. Further, stent 210 may be formed of a single knitted or crocheted wire or filament 219, if desired.

In some instances, uncovered region 216 may be defined as a tissue ingrowth-promoting section of stent 210. Similar to that described above, uncovered region 216 may also include interstices or openings 229 which may promote tissue ingrowth into or through interstices 229 of stent 210 to be securely implanted (e.g., permit tissue ingrowth via a hyperplastic response) within a body lumen.

FIG. 7 further illustrates that first region 215 may define a covered region including covering layer 220 and biodegradable layer 221 applied on at least a portion of outer surface of covering layer 220. Covered section 215 and uncovered section 216 may include one or more, or a plurality of filaments 219 defining a braid, knit and/or mesh structure. Cover layer 220, which may be formed of a biostable material, may be disposed along first region 215 surrounding the braid, knit and/or mesh structure, to thereby extend across openings in the braid, knit and/or mesh structure. Cover layer 220 may be designed to prevent tissue ingrowth along first region 115. Accordingly, cover layer 220 may allow first section 215 to be more easily removed from an implantation site. Cover member 220 may be formed from a suitable material. For example, cover member 220 may include silicone, polytetrafluoroethylene, polyurethane, or the like, or other materials including those disclosed herein. In some instances, cover member 220 may be disposed along an outer surface of filament(s) 219. In other instances, cover member 220 may be disposed along both an inner and an outer surface of filament(s) 219. In some of these and in other instances, cover member 220 may encapsulate filament(s) 219 or otherwise have filament(s) 219 embedded therein. Coupling cover member 220 to filament(s) 219 may include thermal bonding, molding, inject molding, spray coating, dip coating, extruding, adhering, or the like.

Figure 8:
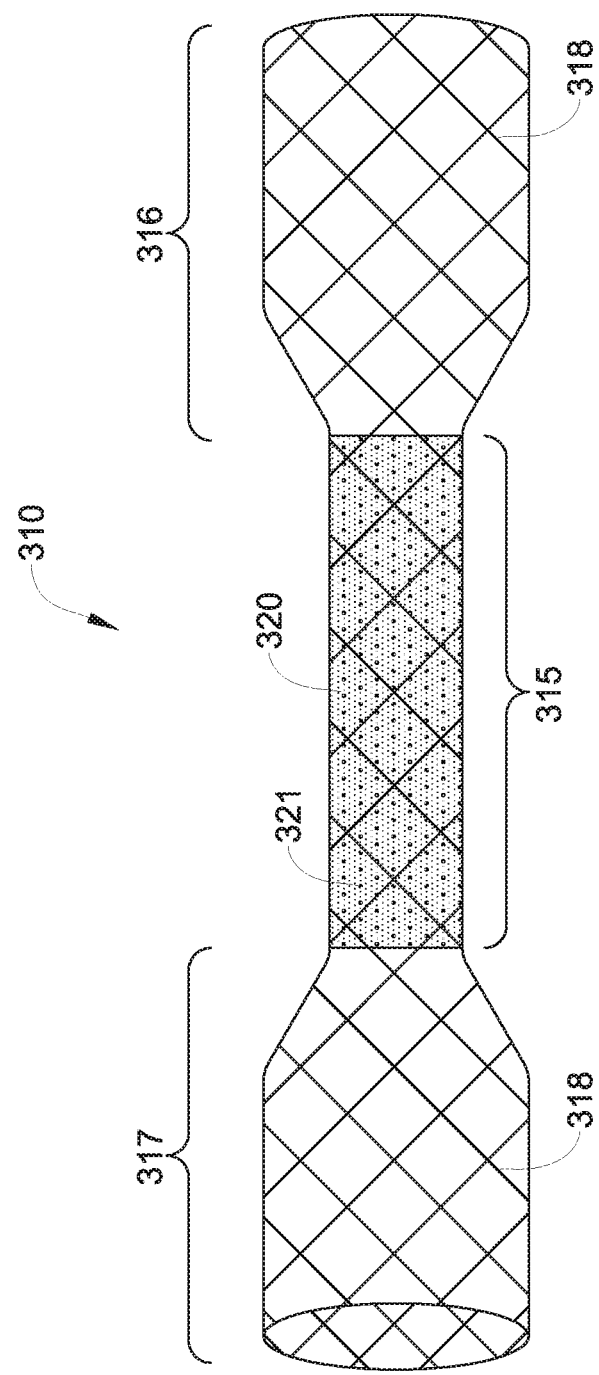
FIG. 8 illustrates another example stent including a covered region and an uncovered region.

FIG. 8 illustrates another example stent 310. Stent 310 may be similar in form and functionality to example stents the portions thereof described above. For example, stent 310 may include stent struts 318 forming an expandable scaffold, a covered, medial region 315 and uncovered end regions 316, 317. In some instances, end regions 316, 317 may be flared regions having a diameter greater than medial region 315. Covered region 315, which may be located intermediate the first uncovered end region 316 and the second uncovered end region 317, may include a biostable covering layer 320 and a biodegradable layer 321 disposed on an outer surface of the biostable covering layer 320 (similar to covering layer 20 and biodegradable layer 21 described above). The uncovered region 317 may be positioned at an end of stent 310 opposite uncovered portion 316. End region 317, may be covered or uncovered. FIG. 8 shows end region 317 uncovered. Additionally, medial region 315, end region 316 and end region 317 may extend along the length of the stent 310 to form an expandable tubular framework with open ends and defining a lumen extending therein.

It is contemplated that any of the stent configurations described herein may include a desiccant and/or similar material as part of the biodegradable layer. The desiccant material may be designed to dry up the lubricious, mucus-like surfaces of the body lumens described herein. By drying up the inner surface of the body lumens, the desiccant material aids the roughened up portion (e.g., portion 23 of layer 20 of stent 10) in gripping the inner surface of the body lumen. An example of a desiccant material may be Mannitol® and/or Hybenx®.

The materials that can be used for the various components of stent 10 (and/or other stents disclosed herein) and the various tubular members disclosed herein may include those commonly associated with medical devices. For simplicity purposes, the following discussion makes reference to stent 10 (and/or other stents disclosed herein) and other components of stent 10 (and/or other stents disclosed herein). However, this is not intended to limit the devices and methods described herein, as the discussion may be applied to other similar tubular members and/or components of tubular members or devices disclosed herein.

Stent 10 (and/or other stents disclosed herein) and/or other components of stent 10 (and/or other stents disclosed herein) may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of stent 10 (and/or other stents disclosed herein) may also be doped with, made of, or otherwise include a radiopaque material. Radiopaque materials are understood to be materials capable of producing a relatively bright image on a fluoroscopy screen or another imaging technique during a medical procedure. This relatively bright image aids the user of stent 10 (and/or other stents disclosed herein) in determining its location. Some examples of radiopaque materials can include, but are not limited to, gold, platinum, palladium, tantalum, tungsten alloy, polymer material loaded with radiopaque filler, and the like. Additionally, other radiopaque marker bands and/or coils may also be incorporated into the design of stent 10 (and/or other stents disclosed herein) to achieve the same result.

In some embodiments, a degree of Magnetic Resonance Imaging (MRI) compatibility is imparted into stent 10 (and/or other stents disclosed herein). For example, stent 10 (and/or other stents disclosed herein), or portions thereof, may be made of a material that does not substantially distort the image and create substantial artifacts (e.g., gaps in the image). Certain ferromagnetic materials, for example, may not be suitable because they may create artifacts in an MRI image. Stent 10 (and/or other stents disclosed herein), or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A medical device for treating a body lumen, comprising:
 an expandable scaffold including a first region and a second region, each of the first and second regions including a plurality of interstices located therein;
 a covering spanning at least a portion of the plurality of interstices of the first region, wherein the covering is formed of a biostable material; and
 a gripping material disposed on at least a portion of the outer surface of the covering, wherein the gripping material is biodegradable and has a roughened surface with a surface roughness value of about 0.5 micrometers (μm) to about 2.5 μm.

2. The medical device of claim 1, wherein the second region is devoid of the covering.

3. The medical device of claim 2, wherein the expandable scaffold is configured to shift from a collapsed state to an expanded state, and when in the expanded state, the gripping material is designed to initially prevent migration of the expandable scaffold in the body lumen until at least a portion of the second region is secured to the inner surface of the body lumen via tissue ingrowth into the interstices of the second region.

4. The medical device of claim 3, wherein the gripping material is configured to degrade over a first time period.

5. The medical device of claim 4, wherein the securement of the second region to the inner surface of the body lumen occurs over a second time period.

6. The medical device of claim 5, wherein the second time period occurs before the first time period.

7. The medical device of claim 5, wherein the second time period overlaps with the first time period.

8. The medical device of claim 7, wherein the second time period is between 4 to 18 days.

9. The medical device of claim 2, further comprising a third region positioned on an end of the scaffold opposite the second region, wherein the third region is devoid of the covering.

10. The medical device of claim 2, wherein the second region includes an endothelializing material disposed along a surface thereof.

11. The medical device of claim 1, wherein the covering is configured to provide a pathway for food to travel therethrough.

12. The medical device of claim 1, wherein the expandable scaffold has a longitudinal axis and a length along the longitudinal axis and wherein the second region has a length which is between 5-15% of the length of the expandable scaffold.

13. The medical device of claim 1, wherein the second region includes a flared portion.

14. A medical device for treating a body lumen, comprising:
 an expandable scaffold including a first region and a second region, each of the first and second regions including a plurality of struts defining a plurality of interstices located therebetween;
 a covering spanning at least a portion of the plurality of interstices of the first region, wherein the covering is biostable; and
 a gripping material disposed on at least a portion of the outer surface of the covering, wherein the gripping material is biodegradable and has a roughened surface with a surface roughness value of about 0.5 micrometers (μm) to about 2.5 μm;
 wherein the expandable scaffold is configured to shift from a collapsed state to an expanded state, and wherein the second region is configured to contact an inner surface of the body lumen in the expanded state;
 wherein the struts of the second region are configured to be secured to the inner surface of the body lumen via tissue ingrowth into the interstices of the second region;
 wherein the gripping material is designed to initially prevent migration of the expandable scaffold upon implantation in the body lumen until the second region is secured to the inner surface of the body lumen.

15. The medical device of claim 14, wherein the struts of the second region are bare metal.

16. The medical device of claim 14, wherein the gripping material is configured to degrade over a first time period.

17. The medical device of claim 16, wherein the securement of the second region to the inner surface of the body lumen occurs over a second time period.

18. The medical device of claim 17, wherein the second time period occurs before the first time period.

19. The medical device of claim 17, wherein the second time period overlaps with the first time period.

20. A method for treating an intestine, the method comprising:
 advancing an expandable scaffold to a target site within the intestine, the expandable scaffold including:
  a first region and a second region, each of the first and second regions including a plurality of interstices located therein;
  a covering spanning at least a portion of the plurality of interstices of the first region, and wherein the covering is formed of a biostable material; and
  a gripping material disposed on at least a portion of the outer surface of the covering, wherein the gripping material is biodegradable and has a roughened surface with a surface roughness value of about 0.5 micrometers (μm) to about 2.5 μm;
 radially expanding the scaffold from the contracted state to the expanded state such that the second region is configured to contact an inner surface of the intestine in the expanded state;
 temporarily securing the inner surface of the first region to the inner surface of the intestine with the gripping material until the second region is secured to the inner surface of the intestine via tissue ingrowth into the interstices of the second region.

\* \* \* \* \*